United States Patent [19]
Wu et al.

[11] Patent Number: 6,015,931
[45] Date of Patent: Jan. 18, 2000

[54] PROCESS TO CONVERT PROPANE INTO ETHYLENE PROPENE AND $C_4$ OLEFINS

[75] Inventors: An-hsiang Wu, Bartlesville; Charles A. Drake, Nowata, both of Okla.

[73] Assignee: Phillips Petroleum Company

[21] Appl. No.: 09/179,774

[22] Filed: Oct. 27, 1998

[51] Int. Cl.[7] .............. C07C 4/02; C07C 5/333
[52] U.S. Cl. ............ 585/649; 585/651; 585/653; 585/660; 585/661
[58] Field of Search .................... 585/649, 651, 585/653, 660, 661

[56] References Cited

U.S. PATENT DOCUMENTS

| | | | |
|---|---|---|---|
| 4,485,185 | 11/1984 | Onodera et al. | 502/71 |
| 4,621,163 | 11/1986 | Kolts | 585/651 |
| 4,631,123 | 12/1986 | Buss et al. | 208/138 |
| 4,721,695 | 1/1988 | Buss et al. | 502/66 |
| 4,929,790 | 5/1990 | Kaeding et al. | 585/651 |
| 4,929,791 | 5/1990 | Kaeding | 585/651 |
| 5,028,312 | 7/1991 | Miller et al. | 208/138 |

*Primary Examiner*—Walter D. Griffin
*Assistant Examiner*—In Suk Bullock
*Attorney, Agent, or Firm*—Richmond, Hitchcock, Fish & Dollar

[57] ABSTRACT

A process to convert propane into ethylene, propene, and $C_4$ olefins, is provided. This process comprises: contacting propane with a composition under converting conditions.

6 Claims, No Drawings

PROCESS TO CONVERT PROPANE INTO ETHYLENE PROPENE AND $C_4$ OLEFINS

FIELD OF THE INVENTION

This invention is related to the field of processes that are used to convert propane into ethylene, propene, and $C_4$ olefins.

BACKGROUND OF THE INVENTION

The production of olefinic compounds is a multimillion dollar business. Millions of dollars have been spent on research to improve these production processes. This is because of the large scale economics that are involved. That is, even small improvements in these processes can add millions of dollars to the bottom line. Consequently, research is on-going to find new and useful ways to produce these higher value olefinic compounds from propane.

SUMMARY OF THE INVENTION

It is an object of this invention to provide a process to convert propane into ethylene, propene, and $C_4$ olefins.

In accordance with this invention said process comprises (or optionally, "consists essentially of", or "consists o"): contacting said propane with a composition under converting conditions;
where said composition comprises
a zeolite component
at least one Group 2 metal,
at least one metal selected from the group consisting of Group 8, Group 9, or Group 10 metals,
a binder component, and
where said converting conditions comprise
a temperature from about 100° C. to about 1000° C., and
a pressure from sub-atmospheric to super-atmospheric.

These and other objects will become more apparent from the following.

The terms "comprise", "comprises", and "comprising" are open-ended and do not exclude the presence of other steps, elements, or materials that are not specifically mentioned in this specification.

The phrases "consists of" and "consisting of" are closed ended and do exclude the presence of other steps, elements, or materials that are not specifically mentioned in this specification, however, they do not exclude impurities normally associated with the elements and materials used.

The phrases "consists essentially of" and "consisting essentially of" do not exclude the presence of other steps, elements, or materials that are not specifically mentioned in this specification, as along as such steps, elements, or materials, do not affect the basic and novel characteristics of the invention, additionally, they do not exclude impurities normally associated with the elements and materials used.

The above terms and phrases are intended for use in areas outside of U.S. jurisdiction. Within the U.S. jurisdiction the above terms and phrases are to be applied as they are construed by U.S. courts and the U.S. Patent Office.

DETAIL DESCRIPTION OF THE INVENTION

The zeolite component comprises a zeolite that has been treated with an acid to form an acid treated zeolite (sometimes called HZSM). Methods of making such acid treated zeolites are known in the art. The zeolite component preferably has a constraint index from about 0.1 to about 12. However, it is preferred when the constraint index is from about 2 to about 9. The constraint index can be determined in accordance with procedures known in the art, preferably, in accordance with U.S. Pat. No. 4,097,367. Examples of zeolites include, but are limited to, ZSM-5; ZSM-8, ZSM-11, ZSM-12, ZSM-35, and ZSM-38. Mixtures of these zeolites can be used. Currently, it is preferred to use ZSM-5 in the form of HZSM-5.

The Group 2 metal is selected from the group consisting of beryllium, magnesium, calcium, strontium, barium, and radium.

The Group 8, Group 9, and Group 10 metal is selected from the group consisting of iron, ruthenium, osmium, cobalt, rhodium, iridium, nickel, palladium, and platinum.

The binder component comprises a compound that is an oxide, or a compound that is convertible to a oxide, where said oxide contains a Group 13–15 element (See Hawley's Condensed Chemical Dictionary, 11th Edition, 1987). Examples of such binder components are chlorhydrol, alumina, silica, aluminum phosphate, and clays. Mixtures of these binder components can be used. Currently it is preferred to use Ludox AS-40 which is silica in water and which is available from the DuPont Company. Examples of the elements that can be used in this invention boron, aluminum, silicon, and phosphorus.

The amount of the Group 2 metal in the composition is from about 0.1 to about 10 weight percent, preferably from about 0.2 to about 5 weight percent, and most preferably from about 0.5 to 2 weight percent, where said weight percent is based on the weight of the composition.

The amount of the Group 8, 9, and 10 metal in the composition is from about 0.1 to about 10 weight percent, preferably from about 0.2 to about 5 weight percent, and most preferably from about 0.5 to 2 weight percent, where said weight percent is based on the weight of the composition.

The amount of binder component to use to form the composition is from about 1 to about 10000 weight percent, preferably from about 10 to about 500 weight percent, and most preferably from about 50 to 150 weight percent, where said weight percent is based on the weight of the zeolite component.

The converting conditions comprise a temperature from about 100° C. to about 1000° C., preferably from about 200° C. to about 900° C., and most preferably from 300° C. to 700° C., a pressure from below atmospheric to super-atmospheric, however, atmospheric is preferred, and a time period for contacting from about 0.1 to about 100 hours, preferably 0.1 to 100 seconds.

EXAMPLES

These examples are provided to illustrate the invention. All parts are parts by weight.

Example One (Inventive)

Fifty parts of a zeolite component that comprised HZSM-5 (purchased from CU Chemie Uetikon, Switzerland, trademark Zeocat® PZ-2/50H), 10 parts of $Ba(NO_3)_2$, and 500 parts of $H_2O$ were mixed together to form a first mixture. This first mixture was then treated to produce a second mixture. This treating was conducted by subjecting the first mixture to a temperature of about 90° C., at about atmospheric pressure, for about 24 hours, followed by filtering and washing with water, and then subjecting the first mixture to a temperature of about 538° C., at about atmospheric pressure, for about 4 hours. Forty-two parts of the second mixture was then mixed with 42 parts of Ludex AS-40, and then extruded into 1/16 inch extrudates, to form a third mixture. This third mixture was then treated to produce a fourth mixture. This treating was conducted by subjecting the third mixture to a temperature of about 125° C., at about atmospheric pressure, for about 3 hours, followed by subjecting the third mixture to a temperature of about 538° C., at about atmospheric pressure, for about 6 hours. The fourth mixture contained 2.0 weight percent Ba based on the weight of the fourth mixture. Three parts of the fourth mixture was then mixed with 1.92 parts of a solution to produce a fifth mixture. This solution contained 1 weight percent chloroplatinic acid and 1 weight percent hydrochloric acid where said weight percent is based on the weight of the solution. This fifth mixture was then treated to form the composition. This treating was conducted by subjecting the fifth mixture to a temperature of about 538° C., at about atmospheric pressure, for about 6 hours. The composition weighted about 2.86 parts. The composition was then used to convert propane to ethylene, propene, and $C_4$ olefins. The results are presented in Table A.

Example Two (Comparative)

Twenty-five parts of a zeolite component that comprised HZSM-5 (purchased from CU Chemie Uetikon, Switzerland, trademark Zeocat® PZ-2/50H), twenty-five parts of Ludex AS-40, and 50 parts of $H_2O$ were mixed together, and then extruded into 1/16 inch extrudates, to form a first mixture. This first mixture was then treated to produce a second mixture. This treating was conducted by subjecting the first mixture to a temperature of about 125° C., at about atmospheric pressure, for about 3 hours, followed by subjecting the first mixture to a temperature of about 538° C., at about atmospheric pressure, for about 6 hours. Seventeen parts of the second mixture was then mixed with 10.27 parts of a solution to produce a third mixture. This solution contained 1 weight percent chloroplatinic acid and 1 weight percent hydrochloric acid where said weight percent is based on the weight of the solution. This third mixture was then treated to form the comparative composition. This treating was conducted by subjecting the third mixture to a temperature of about 538° C., at about atmospheric pressure, for about 6 hours. The composition weighted about 16.65 parts. The composition was then used to convert propane to ethylene, propene, and $C_4$ olefins. The results are presented in Table A

TABLE A

| Example Number | Barium[1] | Platinum[2] | Time on stream[3] | Temperature[4] | Propane Conversion[5] | Yield[6] | Selectivity[7] |
|---|---|---|---|---|---|---|---|
| 1 | 2.0 | 0.255 | 6.5 | 550 | 45.227 | 11.319 | 25.027 |
| 2 | 0.0 | 0.234 | 7.2 | 549 | 74.452 | 4.884 | 6.560 |

[1]This is the weight percent of Barium based on the weight of the composition.
[2]This is the weight percent of Platinum based on the weight of the composition.
[3]Time on stream in hours.
[4]Temperature in ° C. The reaction was run at about atmospheric pressure.
[5]The is the weight percent of propane converted to other compounds based on the total weight propane used in the reaction.
[6]This is the weight percent of ethylene, propene, and $C_4$ olefins, that was produced based on the weight of propane converted.
[7]This is the (yield * 100)/propane conversion.

That which is claimed is:

1. A process to convert propane into ethylene, propene, and $C_4$ olefins, said process comprising: contacting said propane with a composition under converting conditions;

where said composition comprises
      a zeolite component
      at least one Group 2 metal,
      at least one metal selected from the group consisting of Group 8, Group 9, or Group 10 metals,
      a binder component, and
   where said converting conditions comprise
      a temperature from about 100° C. to about 1000° C., and
      a pressure from sub-atmospheric to super-atmospheric.

2. A process according to claim 1 wherein said zeolite component has constraint index from about 2 to about 9.

3. A process according to claim 2 wherein said Group 2 metal is barium.

4. A process according to claim 3 wherein said Group 10 metal is platinum.

5. A process according to claim 4 wherein said binder component is silica.

6. A process according to claim 5 wherein said zeolite component comprises HZSM-5.

* * * * *